(12) United States Patent
Mahfouz et al.

(10) Patent No.: US 10,508,240 B2
(45) Date of Patent: Dec. 17, 2019

(54) INTEGRATED THERMAL PROCESSING FOR MESOPHASE PITCH PRODUCTION, ASPHALTENE REMOVAL, AND CRUDE OIL AND RESIDUE UPGRADING

(71) Applicant: Saudi Arabian Oil Company, Dhahran (SA)

(72) Inventors: Remi Mahfouz, Thuwal (SA); Faisal Melibari, Thuwal (SA); Mohammed A. Al-Daous, Thuwal (SA); Wei Xu, Thuwal (SA)

(73) Assignee: Saudi Arabian Oil Company, Dhahran (SA)

( * ) Notice: Subject to any disclaimer, the term of this patent is extended or adjusted under 35 U.S.C. 154(b) by 228 days.

(21) Appl. No.: 15/626,726

(22) Filed: Jun. 19, 2017

(65) Prior Publication Data

US 2018/0362855 A1    Dec. 20, 2018

(51) Int. Cl.
| | | |
|---|---|---|
| *C10C 3/00* | (2006.01) | |
| *C01B 21/00* | (2006.01) | |
| *B01J 8/10* | (2006.01) | |
| *C10G 21/00* | (2006.01) | |
| *G01N 23/20* | (2018.01) | |
| *D01F 9/14* | (2006.01) | |

(52) U.S. Cl.
CPC ............... *C10C 3/002* (2013.01); *B01J 8/10* (2013.01); *C01B 21/00* (2013.01); *C10C 3/00* (2013.01); *C10G 21/003* (2013.01); *D01F 9/14* (2013.01); *G01N 23/20075* (2013.01)

(58) Field of Classification Search
CPC .......... C10C 3/00; C10C 3/002; C10G 21/003
See application file for complete search history.

(56) References Cited

U.S. PATENT DOCUMENTS

| | | |
|---|---|---|
| 1,842,105 A | 1/1932 | Loomis |
| 3,617,493 A | 11/1971 | Wirth et al. |
| 3,974,264 A | 8/1976 | McHenry |
| 4,026,788 A | 5/1977 | McHenry |

(Continued)

FOREIGN PATENT DOCUMENTS

| | | |
|---|---|---|
| CN | 104498072 A | 4/2015 |
| CN | 104818041 A | 8/2015 |

(Continued)

OTHER PUBLICATIONS

International Search Report and Written Opinion for related PCT application PCT/US2018/049925 dated Nov. 15, 2018.

(Continued)

*Primary Examiner* — Renee Robinson
*Assistant Examiner* — Derek N Mueller
(74) *Attorney, Agent, or Firm* — Bracewell LLP; Constance G. Rhebergen; Kevin R. Tamm

(57) ABSTRACT

A method for producing mesophase pitch includes the steps of flushing a vessel with an at least substantially inert gas to remove air and oxygen from the vessel; charging the vessel with a hydrocarbon feed; pressurizing the vessel to an initial increased pressure; heating the vessel to a pre-determined temperature; and maintaining the vessel at the pre-determined temperature for an amount of time operable to upgrade the hydrocarbon feed to a product comprising mesophase pitch.

20 Claims, 6 Drawing Sheets

(56) References Cited

U.S. PATENT DOCUMENTS

| | | | |
|---|---|---|---|
| 4,049,538 A | 9/1977 | Hayashi et al. | |
| 4,134,824 A | 1/1979 | Kamm et al. | |
| 4,209,500 A | 6/1980 | Chwastiak | |
| 4,217,204 A | 8/1980 | Sakai et al. | |
| 4,303,631 A | 12/1981 | Lewis et al. | |
| 4,317,809 A | 3/1982 | Lewis et al. | |
| 4,426,278 A | 1/1984 | Kosters | |
| 4,551,225 A | 11/1985 | Dickakian | |
| 4,801,372 A | 1/1989 | Tate et al. | |
| 4,892,641 A * | 1/1990 | Fu ........................ | C10C 3/002 208/39 |
| 4,904,371 A | 2/1990 | Kalback | |
| 4,931,162 A | 6/1990 | Romine | |
| 5,198,101 A | 3/1993 | Kalback | |
| 5,259,947 A | 11/1993 | Kalback | |
| 5,437,780 A | 8/1995 | Southard et al. | |
| 5,540,832 A | 7/1996 | Romino | |
| 5,540,903 A | 7/1996 | Romine | |
| 6,632,351 B1 | 10/2003 | Ngan et al. | |
| 6,979,757 B2 | 12/2005 | Powers | |
| 7,285,697 B2 | 10/2007 | Keusenkothen | |
| 7,311,746 B2 | 12/2007 | Stell et al. | |
| 7,381,320 B2 | 6/2008 | Iqbal et al. | |
| 7,404,889 B1 | 7/2008 | Powers | |
| 7,744,747 B2 | 6/2010 | Halsey | |
| 7,790,018 B2 | 9/2010 | Khan | |
| 7,972,498 B2 | 7/2011 | Buchanan et al. | |
| 9,284,499 B2 | 3/2016 | Van Wees et al. | |
| 9,382,486 B2 | 7/2016 | Bourane et al. | |
| 9,580,839 B2 | 2/2017 | Bohnert et al. | |
| 2008/0277314 A1 | 11/2008 | Halsey | |
| 2009/0050523 A1 | 2/2009 | Halsey | |
| 2015/0076031 A1 | 3/2015 | Zhao et al. | |

FOREIGN PATENT DOCUMENTS

| | | |
|---|---|---|
| CN | 105238430 A | 1/2016 |
| CN | 105238431 A | 1/2016 |
| DE | 3841677 A1 | 6/1990 |
| JP | S59128208 A | 7/1984 |
| JP | 6312689 | 1/1988 |
| WO | 0063320 A1 | 10/2000 |

OTHER PUBLICATIONS

Gonzalo Leal, et al., "Production of Carbon Fibers from Castilla's Crude-Oil Deasphalted Bottoms," Ciencia, Tecnologia y Futuro, Dec. 2002, vol. 2, No. 3, pp. 41-47.

Yong-Ki Park, et al., "Catalytic Cracking of Lower-Valued Hydrocarbons for Producing Light Olefins," Catalysis Surveys, Asia, 2010, 14( 2), pp. 75-84.

Ming Li, et al.,"Preparation of the Mesophase Pitch by Hydrocracking Tail Oil from a Naphthenic Vacuum Residue" Energy & Fuels, 2015, 29(7), pp. 4193-4200.

International Search Report and Written Opinion for related PCT application PCT/US2018/038231 dated Sep. 26, 2018.

* cited by examiner

INTEGRATED THERMAL PROCESSING FOR MESOPHASE PITCH PRODUCTION, ASPHALTENE REMOVAL, AND CRUDE OIL AND RESIDUE UPGRADING

BACKGROUND

Field

Embodiments of the disclosure relate to upgrading crude oil and crude oil residues. In particular, embodiments of the disclosure relate to upgrading crude oil and crude oil residues to produce mesophase pitch.

Description of the Related Art

Crude oil and crude oil residues can be processed through energy intensive refining processes to produce mesophase pitch. The condensed aromatic nature of pitches provides thermal stability, such that mesophase pitch can be melt spun for use in carbon fiber applications. In some instances, melt spinning is preferred to wet/dry spinning, which is used in the production of polyacrylonitrile-(PAN) based fibers and involves large quantities of solvents and waste byproducts. High quality carbon fibers can be produced from optically anisotropic or mesophase pitch (MP), but production of this carbon fiber precursor has required extensive refining and complicated processing, which has made producing carbon fibers from mesophase pitch less desirable than producing PAN-based carbon fibers.

Carbon fibers combine high strength and tensile modulus with other desirable properties such as being lightweight, being chemically inert, having low thermal expansion, and having superior electrical and thermal conductivities. Smaller structural flaws in fiber form and enhanced molecular orientation allow for these properties and make carbon fibers suitable for a number of structural and functional applications.

One challenge, however, to producing carbon fibers from mesophase pitch in a direct crude-oil-to-chemicals (C2C) technology is that about 10-15% of highly viscous hydrotreated (HT) residues produced during crude oil processing (the greater than about 500° C. "cut," or greater than about 500° C. boiling point) will be wasted. Therefore, processing crude oils and crude oil residues to produce mesophase pitch, which has a lower boiling point, is desirable, so it can be used to produce carbon fibers, used as gas oil directly, and used as a feedstock for a cracking process such as fluidized catalytic cracking (FCC).

SUMMARY

The disclosure presents thermal treatment systems and methods for the production of high quality mesophase pitch (MP) directly from crude oils or crude oil residues with or without hydrotreating, with simultaneous removal of asphaltenes, which decrease the viscosity and boiling point of heavy crude oils or residues. The solid, liquid, and gas portions of products of such systems and methods can be fractionated into refinery products and used as feeds for direct C2C processes, including steam cracking processes and catalytic cracking processes.

Developing lower-cost mesophase pitch precursors in high volume allows for lower-cost carbon fiber production for use in multiple industries. Low-cost mesophase pitch production, in some embodiments of the disclosure without or in the absence of non-inert chemical additives such as solvents, can beneficially impact the carbon fiber industry. For example, low-cost carbon fiber based pipelines could be used to transport crude oil and its refinery products, which will help eliminate corrosion damage and production interruptions. In addition, direct production of mesophase pitch from crude oil or crude oil residues, rather than mesophase pitch production from commercial pitch, would allow for elimination of costly refining process steps.

Therefore, disclosed here is a method for producing mesophase pitch, the method including the steps of flushing a vessel with an at least substantially inert gas to remove air and oxygen from the vessel; charging the vessel with a hydrocarbon feed; pressurizing the vessel to an initial increased pressure; heating the vessel to a pre-determined temperature; and maintaining the vessel proximate the pre-determined temperature for an amount of time operable to upgrade the hydrocarbon feed to a product comprising mesophase pitch. In some embodiments, the hydrocarbon feed comprises at least one hydrocarbon selected from the group consisting of: heavy crude oil, light crude oil, and crude oil residue with a boiling point greater than about 500° C. In other embodiments, the step of pressurizing the vessel to the initial increased pressure includes pressurizing the vessel with the at least substantially inert gas. Still in other embodiments, the at least substantially inert gas includes nitrogen.

In other embodiments of the method, the pre-determined temperature is between about 350° C. and about 450° C. Still in other embodiments, the pre-determined temperature is between about 400° C. and about 425° C. In certain embodiments, the initial increased pressure is between about 290 psig and about 725 psig. In some embodiments, the initial increased pressure is between about 550 psig and about 600 psig. In other embodiments, the amount of time is between about 6 hours and about 17 hours. Still in yet other embodiments of the method, the pre-determined temperature is about 425° C., the initial increased pressure is about 600 pounds per square inch gauge (psig), and the amount of time is about 6 hours.

In certain embodiments, an asphaltene compound content of the product is reduced by at least about 50% by mass relative to the hydrocarbon feed. Still in other embodiments, an asphaltene compound content of the product is reduced by at least about 90% by mass relative to the hydrocarbon feed. In yet other embodiments, the steps of the method are carried out without applying any additional additives or solvents. In some embodiments, a metal content in a liquid phase of the product comprising mesophase pitch is less than a metal content in the hydrocarbon feed. Still in other embodiments, the product comprising mesophase pitch is homogeneous throughout a liquid phase and is suitable for direct crude-to-chemical applications.

Still in other embodiments, the product comprising mesophase pitch includes a distinct solid phase that is at least about 90% pure mesophase pitch. In certain embodiments, the product comprising mesophase pitch includes a distinct solid phase that is at least about 99% pure mesophase pitch. Still in other embodiments, the product comprising mesophase pitch includes a distinct liquid phase where about 80% by mass of the liquid phase exhibits a boiling point less than about 250° C. In yet other embodiments, the product comprising mesophase pitch includes a distinct liquid phase where about 90% by mass of the liquid phase exhibits a boiling point less than about 400° C. Still in other embodiments, the product comprising mesophase pitch includes a distinct liquid phase where about 90% by mass of the liquid phase exhibits a boiling point less than about 500° C.

In further embodiments, the step of maintaining the vessel at the pre-determined temperature for an amount of time operable to upgrade the hydrocarbon feed to a product comprising mesophase pitch increases the initial increased pressure in the vessel to between about 1,700 psig and about 2,500 psig.

BRIEF DESCRIPTION OF THE DRAWINGS

These and other features, aspects, and advantages of the present disclosure will become better understood with regard to the following descriptions, claims, and accompanying drawings. It is to be noted, however, that the drawings illustrate only several embodiments of the disclosure and are therefore not to be considered limiting of the disclosure's scope as it can admit to other equally effective embodiments.

DETAILED DESCRIPTION

So that the manner in which the features and advantages of the embodiments of systems and methods of integrated thermal processing for mesophase pitch production, asphaltene removal, and crude oil and residue upgrading, as well as others, which will become apparent, may be understood in more detail, a more particular description of the embodiments of the present disclosure briefly summarized previously may be had by reference to the embodiments thereof, which are illustrated in the appended drawings, which form a part of this specification. It is to be noted, however, that the drawings illustrate only various embodiments of the disclosure and are therefore not to be considered limiting of the present disclosure's scope, as it may include other effective embodiments as well.

The American Petroleum Institute (API) gravity is a measure of how "heavy" or "light" a petroleum liquid is. The relationship between API gravity and specific gravity (SG) at 60° F. is API=(141.5/SG)−131.5. Crude oil from Saudi Arabia with API gravity higher than about 32 is called Arabian light or "AL" and crude oil with API gravity lower than about 28 is called Arabian heavy or "AH." Throughout the present disclosure, hydrotreated ("HT") residue of Arabian light crude oil is also referred to as "C2C" (crude-to-chemical) rejects, and the terms identify the residue obtained with a boiling point greater than about 500° C. after hydrotreating Arabian light crude oil.

Figure 1A:
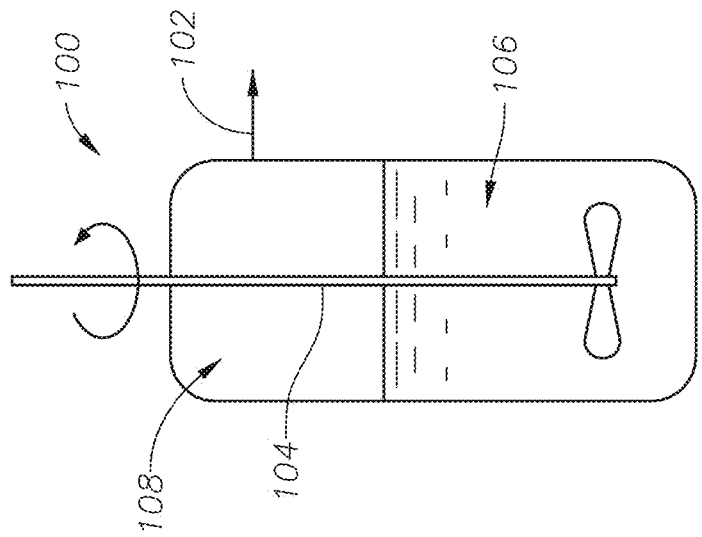
FIG. 1A is a diagram showing a device suitable for upgrading crude oil and crude oil residues to mesophase pitch in embodiments of the disclosure.

Referring first to FIG. 1A, a diagram is provided showing a device suitable for upgrading crude oil and crude oil residues in embodiments of the disclosure. Device 100 includes an autoclave 102 with a stir bar 104, and a crude oil or crude oil residue sample 106 is shown disposed within autoclave 102. Autoclave 102 can be heated consistently up to a certain pre-determined or pre-set temperature. Once heated to a pre-set temperature, autoclave 102 can be maintained isothermally in addition to or alternative to isobarically. Stir bar 104 can be operational either or both during the period of heating up to a certain pre-determined or pre-set temperature and while the autoclave is maintained at a pre-determined or pre-set temperature for a pre-determined amount of time.

For example, in some embodiments, autoclave 102 can be heated between about 1° Centigrade (° C.)/minute (min) and about 10° C./min to a temperature between about 360° C. and about 500° C. In some embodiments, autoclave 102 is heated to about between 400° C. and 425° C. Autoclave 102 shows a voidspace 108 above crude oil or crude oil residue sample 106, which in certain embodiments includes nitrogen gas in addition to or alternative to one or more inert gases, for example argon or helium.

Nitrogen in addition to or alternative to one or more inert gases can be used to maintain an increased pressure in autoclave 102, for example between about 290 pounds per square inch gauge (psig) and about 725 psig. In some embodiments, the pressure within autoclave 102 is maintained at about 600 psig using nitrogen at about room temperature. In certain embodiments, during heat treatment, the pressure in a high pressure vessel, such as autoclave 102, can reach between about 1700 psig to about 2500 psig, depending on the volume of the starting feed, the volume of a voidspace, and temperature during treatment.

The speed of stir bar 104 can be adjusted. In some embodiments, the stir bar is adjustable between about 0 and about 700 rotations per minute (rpm), and in some embodiments the speed of the stir bar is set at about 650 rpm during a period where the autoclave is heating to a pre-determined or pre-set temperature. In some embodiments, stirring is continuous during an entire treatment, for example while pressure in a pressure vessel increases to between about 1700 psig to about 2500 psig. Additionally, the volume of voidspace 108 above crude oil or crude oil residue sample 106 and the volume of the crude oil or crude oil residue sample 106 can be adjusted to affect the treatment method and the ability of the treatment method to lower the boiling point of a treated sample.

Figure 1B:
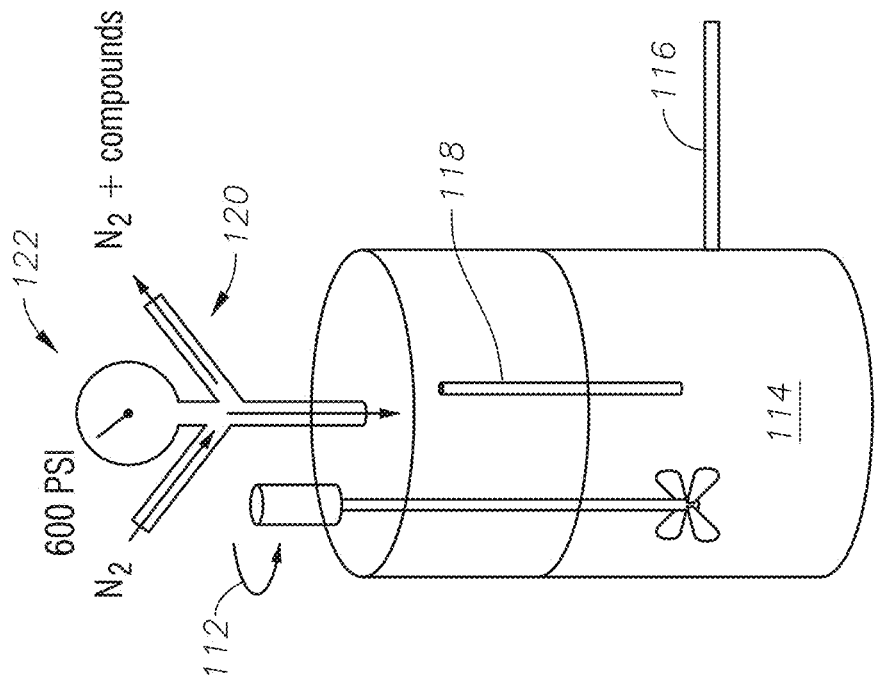
FIG. 1B is a diagram showing an experimental set-up used to exemplify certain embodiments of producing mesophase pitch.

FIG. 1B is a diagram showing an experimental set-up used to exemplify certain embodiments of producing mesophase pitch, and is similar to the autoclave 102 described for FIG. 1A. An autoclave 110 includes a stir bar 112, which is used to stir a crude oil or crude oil residue sample 114. Crude oil or crude oil residue sample 114 can include Arabian heavy crude oil and hydrotreated (HT) rejects from Arabian light crude (C2C rejects). Autoclave 110 includes an outer thermocouple 116 and an inner thermocouple 118 for accurately measuring the temperature of crude oil or crude oil residue sample 114.

As pictured, a venting apparatus 120 allows nitrogen gas to enter autoclave 110 and maintain the internal pressure at about 600 psi (as shown on pressure gauge 122), for example at about room temperature, and venting apparatus 120 allows nitrogen gas and certain reaction compounds to be vented and exit autoclave 110. In some embodiments, the temperature is maintained between about 400° C. and about 425° C. for between about 6 hours and about 17 hours during treatment. In some embodiments, the temperature is maintained between about 350° C. and about 450° C. for between about 1 and about 15 hours. Any oxygen present in the autoclave 110 or crude oil residue sample 106 should be evacuated before treatment is applied here.

In some embodiments, a one step process to upgrade Arabian heavy crude oil or crude oil residue to mesophase pitch is applied without, or in the absence of, any pretreatment. Certain mesophase pitch precursors in the present disclosure include, for example, Arabian heavy crude oil and a cut over 500° C. of Arabian light crude hydrothermally treated. The Arabian light cut contains about 60% aromatics compounds. In certain embodiments of the present disclosure, before heating a pressure vessel, such as an autoclave, the pressure vessel is pressurized to about 600 psig (under nitrogen gas, in addition to or alternative to other inert gases), and during heating the pressure within the pressure vessel may reach as high as about 1700 psig to about 2500 psig, for example about 1800 psig, or about 1900 psig, during a soaking time (polymerization time) depending on the temperature of the treatment and the loading of the feed. High pressure and temperature combinations in the present disclosure lead to a one-step process for the conversion of hydrocarbons to mesophase pitch without pretreatment.

Figure 2:
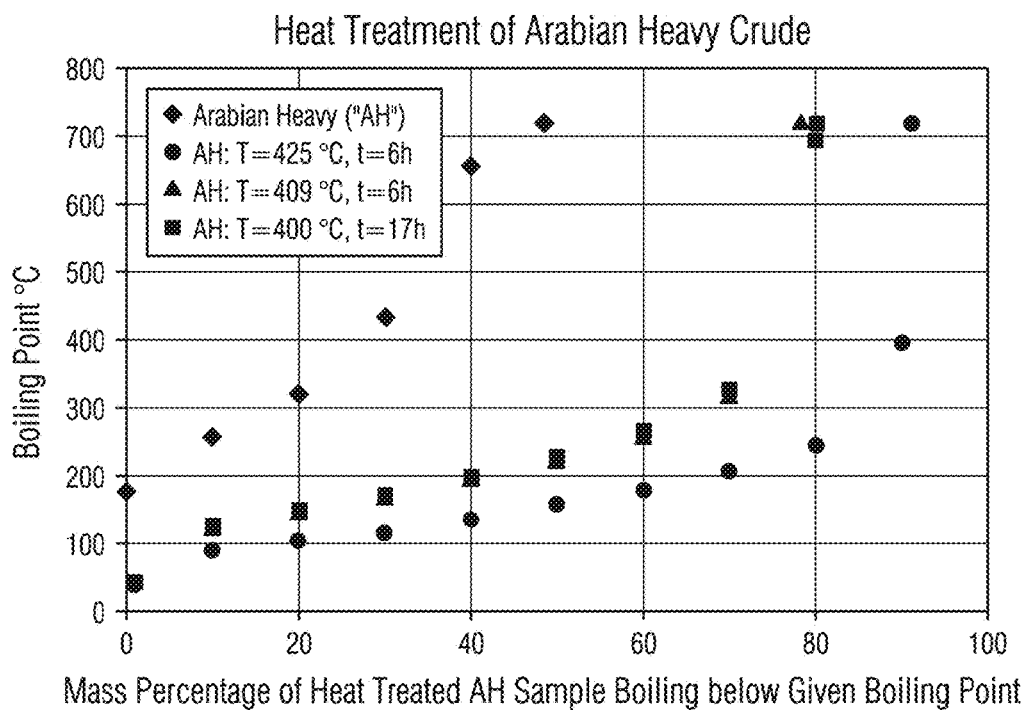
FIG. 2 is a graph showing the reduction in boiling point for samples of Arabian heavy crude oil which were thermally treated according to embodiments of the present disclosure.

FIG. 2 is a graph showing the reduction in boiling point for samples of Arabian heavy crude oil which were thermally treated according to an embodiment of the present disclosure. In an experiment using Arabian heavy crude oil in a device similar to those described in FIGS. 1A and 1B, a 30 milliliter (mL) feed of Arabian heavy crude was loaded in an autoclave of 100 ml volume, and the autoclave was flushed several times with $N_2$ gas to remove any oxygen and air content in the autoclave. The autoclave was maintained under $N_2$ pressure at about 600 psig at room temperature. Samples were then heated at the temperatures and for the amounts of time shown in FIG. 2. FIG. 2 shows the mass percentage of the liquid cut of the heat treated Arabian heavy sample boiling at less than a given boiling point. The liquid cut of obtained product from the Arabian heavy crude precursor represents about 80% by mass of the obtained product.

Figure 9:
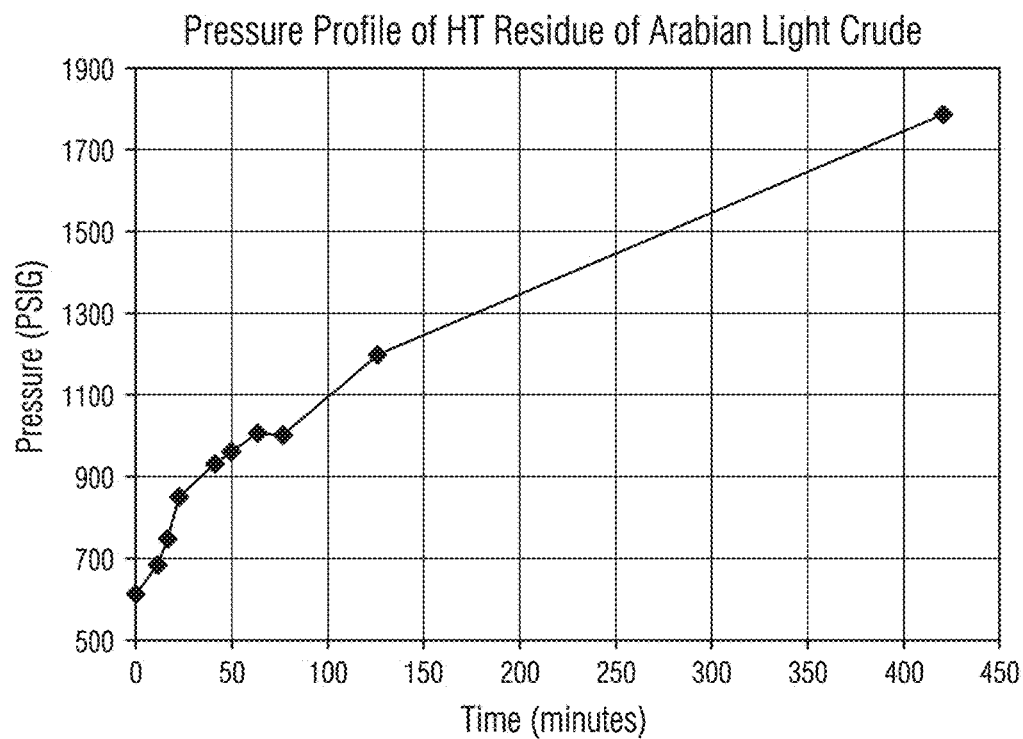
FIG. 9 is a graph showing the pressure profile of a reactor vessel during heat treatment of HT residue of Arabian light crude oil.
Figure 10:
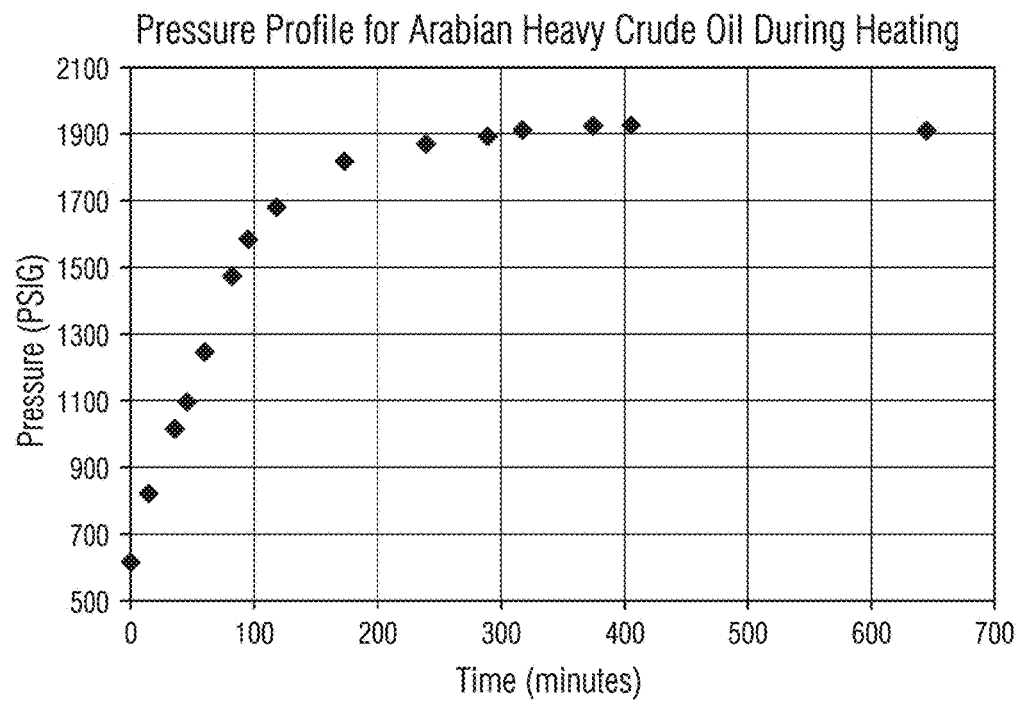
FIG. 10 is a graph showing the pressure profile of a reactor vessel during heat treatment of Arabian heavy crude oil.

While the initial pressure of a treatment reactor such as an autoclave is about 600 psig at room temperature, as FIGS. 9 and 10 show, pressure within a treatment reactor such as an autoclave increases dramatically, and in some embodiments increases to about between 1,700 psig and about 2,500 psig, in some embodiments between about 1,900 psig and about 2,100 psig, in some embodiments to about 1,850 psig, and in some embodiments to about 1,900 psig.

Figure 4:
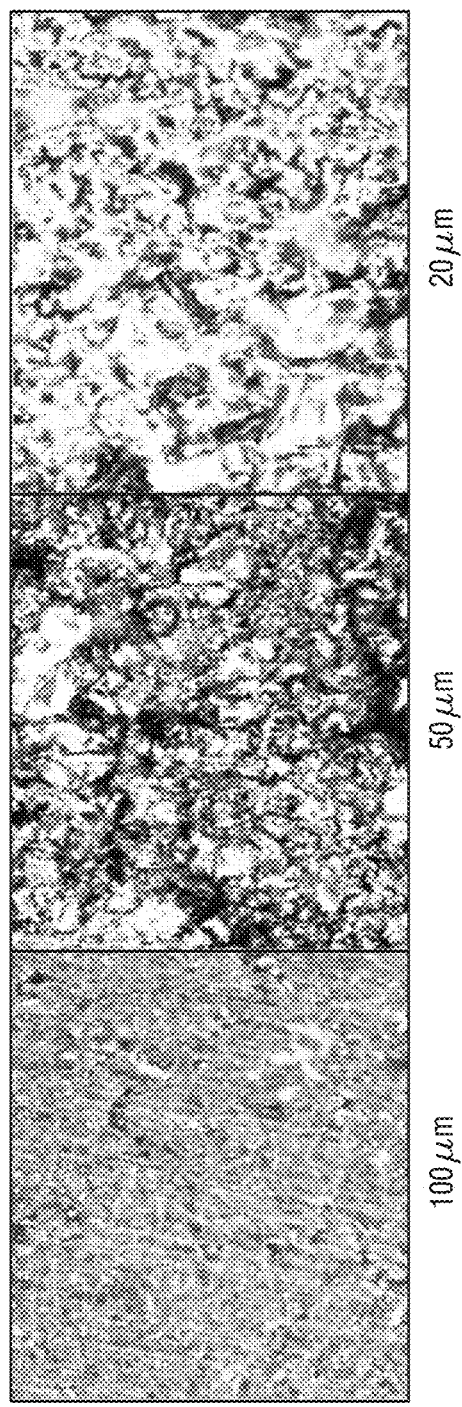
FIG. 4 shows optical microscope images of mesophase pitch obtained using embodiments of the present disclosure at 100 μm, 50 μm, and 20 μm scales, where crude oil and crude oil residue samples were treated at a temperature of 425° C., and at a stirring rate of 650 rotations per minute (rpm) for 6 hours.

The desired mesophase pitch product is homogeneous (as shown in FIG. 4 and discussed further as follows), solid at room temperature, and represents about 100% of the carbon fraction of the solid obtained after the process. The softening point of the mesophase pitch is preferably about 200° C., and in some embodiments is between about 200° C. and 350° C. This range of temperatures for the softening point of mesophase pitch allows for the use of the product in melt spinning production of carbon fibers with advantageous mechanical and thermal properties.

The resulting product in a treatment vessel, for example those shown in FIGS. 1A and 1B, contains a solid phase at room temperature representing about 10 weight percent±5 weight percent of the obtained carbon fraction (depending on the feed, temperature, and time of polymerization). The liquid phase ("cut") represents about 80 weight percent±5 weight percent of the obtained carbon fraction, and the gas phase is about 10 weight percent±5 weight percent of the obtained carbon fraction.

In a series of experiments, the reactor temperature was increased by 6° C./min to pre-determined temperatures of 400° C., 409° C., and 425° C. under stirring at about 650 rpm. When the desired reaction temperature was reached, heat treatment was maintained for the pre-determined or pre-set polymerization time, and the stirring was continuous with rotation at 650 rpm from the period the experimental vessel was at room temperature until the conclusion of the experiment. After heating for either 6 hours or 17 hours as shown in FIG. 2, the obtained product in the autoclave consisted of three separate phases: gas, liquid, and solid. The liquid phase obtained after heating was characterized by simulated distillation (SIMDIS). Required polymerization time refers generally to the soaking time that the reaction requires for forming mesophase pitch to be completed, or in other words it is the time needed for the oil upgrading and mesophase pitch formation. During the heating process, it has been reported that mesophase pitch is formed by polymerization of many aromatic compounds present in crude oil.

The volatilities of different components in the crude oil and residue, and in the heat-treated crude oil and heat-treated residue, were measure by the Agilent Simulated Distillation ("SIMDIS") System by Agilent Technologies of Sugar Land, Tex. SIMDIS follows the standard operating procedure (SOP) described in the reference manual and the method incorporates ASTM D7169.

In certain embodiments of the present technology, thermal treatment is carried out in the absence of or without any additive other than nitrogen in addition to or alternative to one or more inert gases to pressurize the thermal treatment process. In some embodiments, a greater than about 90% pure mesophase pitch product is obtained after thermal treatment, and in some embodiments a greater than about 99% pure mesophase pitch product is obtained after thermal treatment. Crude oil and HT crude oil residues can be upgraded and de-asphalted simultaneously using pressurized thermal treatments of the present disclosure.

Figure 3:
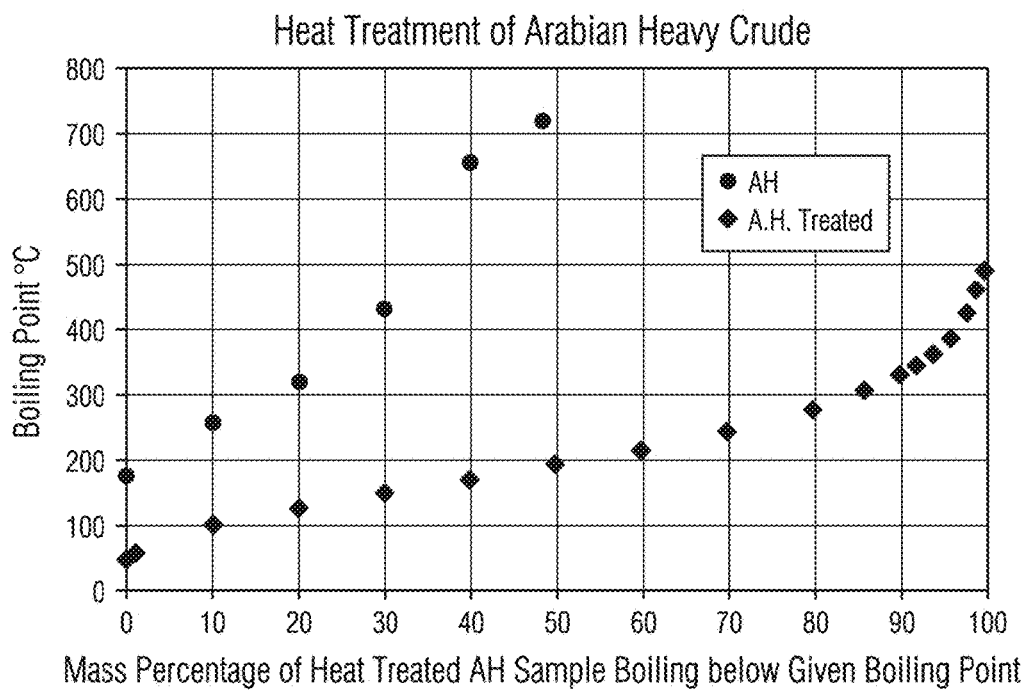
FIG. 3 is a graph showing the reduction in boiling point for a sample of Arabian heavy crude oil which was thermally treated according to an embodiment of the present disclosure at a temperature of 425° C., and at a stirring rate of 650 rotations per minute (rpm) for 6 hours.

FIG. 3 is a graph showing the reduction in boiling point for a sample of Arabian heavy crude oil which was thermally treated according to an embodiment of the present disclosure at a temperature of 425° C., at a stirring rate of 650 rotations per minute (rpm) for 6 hours. High quality mesophase pitch was produced, while asphaltenes in the crude oil were reduced and the American Petroleum Institute (API) number was increased. API numbers for API gravity in embodiments of the present disclosure were measure using method ASTM D287.

FIG. 4 shows optical microscope images of solid mesophase pitch obtained using embodiments of the present disclosure at 100 μm, 50 μm, and 20 μm scales, where the mesophase pitch was obtained after treating a sample at a temperature of 425° C., and at a stirring rate of 650 rotations per minute (rpm) for 6 hours. Mesophase pitch produced using embodiments of the present disclosure is a suitable, high-quality precursor for pitch-based carbon fibers. The mesophase pitch obtained includes a suitable amount of alkyl side chains, lower softening point, and an advantageous, consistent crystalline structure identified using a polarized optical microscope and XRD. The images in FIG. 4 show the mesophase pitch is beneficially homogeneous throughout. Similar results were obtained with optical microscope images for both Arabian heavy and HT residue of Arabian light (C2C reject) starting materials.

The purity of mesophase pitch was determined by the polarized microscope by counting the percentage of the mesophase areas that reflect the light differently than the "non mesophase" areas. The purity of the mesophase pitch in embodiments of the present disclosure can be greater than about 90% and greater than about 99%.

Figure 5:
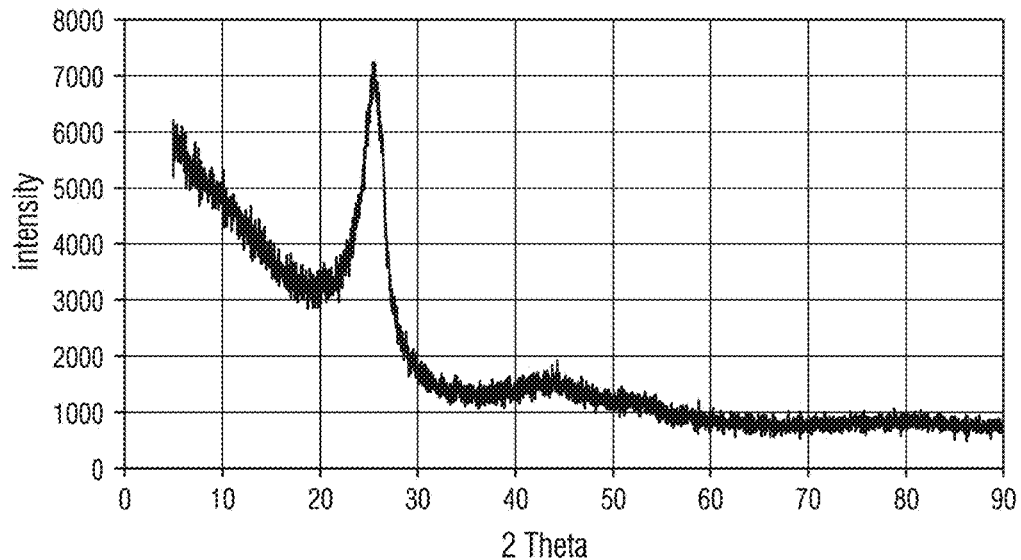
FIG. 5 is a graph showing X-ray diffraction (XRD) data for mesophase pitch obtained using embodiments of the present disclosure, where crude oil and crude oil residue samples were treated at a temperature of 425° C., and at a stirring rate of 650 rotations per minute (rpm) for 6 hours.

FIG. 5 is a graph showing X-ray diffraction (XRD) data for mesophase pitch obtained using embodiments of the present disclosure, where the mesophase pitch was obtained at a temperature of 425° C., and at a stirring rate of 650 rotations per minute (rpm) for 6 hours. The XRD graph shows a peak at 25.6, which identifies mesophase pitch carbon material. Mesophase pitch obtained using the methods described here also contained less asphaltenes than the mesophase pitch precursors, such as crude oil and crude oil residue. In some embodiments, up to about 90% asphaltenes removal was realized and mesophase pitch suitable for C2C applications, such as carbon fibers, was obtained. The final product characterization with XRD shows the usual diffraction graph for mesophase pitch, which is described as going through heated polymerization of aromatic compounds and resin compounds in crude oil into higher molecular weight molecules.

Table 1 shows values for saturated hydrocarbons, aromatics, resins, and asphaltenes for Arabian heavy crude oil, thermally treated Arabian heavy crude oil, hydrotreated crude oil residue, and thermally treated hydrotreated crude oil residue.

TABLE 1

Saturated carbon, aromatic, resin, and asphaltene (SARA) fractions of crude oil and hydrotreated crude oil residue before and after treatment.

| Sample ID | Saturates (wt. %) | Aromatics (wt. %) | Resins (wt. %) | Asphaltene (wt. %) |
| --- | --- | --- | --- | --- |
| Arabian Heavy | 32.4 | 35.4 | 21.8 | 10.8 |
| Arabian Heavy Treated Liquid Cut | 9.57 | 78.3 | 10.94 | 1.19 |
| Arabian Light HT Residue | 31.8 | 60 | 5.1 | 3.1 |
| Arabian Light HT Residue Treated Liquid Cut | 34.6 | 58.4 | 5.2 | 1.8 |

Crude oil or its derivatives can been separated into four chemical group classes, namely saturates such as alkanes and cycloparaffins, aromatics, resins, and asphaltenes, the so-called SARA fractions. SARA analysis is used to determine the distribution of saturates, aromatics, resins, and asphaltene in topped petroleum samples. The procedure is divided into two stages: The first stage involves the precipitation and quantification of asphaltenes, while the second stage is the open-column chromatographic separation of the de-asphalted oil into saturate, aromatic, and resin fractions following the ASTM D-2007 method.

Notably, Table 1 shows that the AH treated product had been de-asphalted, as about 90% of the asphaltene has been removed. As shown in Table 1, a large portion of the asphaltenes content is removed after processing the crude oil. Also shown in Table 1 is the reduction in resins content by about half for Arabian heavy crude. For Arabian heavy, aromatics content increased by more than 100% from 35% to 78%.

Table 2 shows elemental analysis of both Arabian heavy crude oil and its thermally treated product. The mesophase pitch hydrocarbon product obtained also contained much less sulfur, nickel, and other metals, such as for example vanadium, than its precursors, which allows the mesophase pitch to be suitable for direct crude to chemicals technology via either steam cracking or catalytic cracking processes. In the inductively coupled plasma (ICP) mass spectrometer used for detecting metals, the practical quantitation limit (QPL) for the sample weight used (30 milligrams, mg) was: nickel=0.05 mg, sulfur=0.4 mg, and vanadium=0.05 mg.

TABLE 2

Elemental analysis of both Arabian heavy crude oil and its thermally treated product (mesophase pitch).

| Sample ID | Inductively Coupled Plasma (ICP) Mass Spectrometry | Ni (mg) | S (mg) | V (mg) |
| --- | --- | --- | --- | --- |
| Treated Arabian Heavy | Liquid | Not Detected | 2.34 | Not Detected |
| | Solid | 0.0175 | 0.79 | 0.005 |
| Arabian Heavy Crude | Whole | 0.0021 | 3.29 | 0.006 |

As shown in Table 2, the heavy metal content (Ni and V) was not detected in the liquid phase of the obtained product (treated Arabian heavy). The sulfur content in the liquid phase was also significantly decreased. The liquid composition analyzed by SIMDIS showed 100% of the components have a boiling point less than 500° C. after the Arabian heavy oil treatment and 96% of the components have a boiling point less than 500° C. after the residue treatment.

In certain embodiments, different precursors have been tested including Arabian heavy oil and a cut over 500° C. of Arabian light hydrothermally treated. The beginning pressure of a pressure vessel, such as for example an autoclave or any high pressure processing unit, in some embodiments is at least about 600 psig (at room temperature), and then the temperature is raised gradually to about 420° C. During treatment, the pressure in a high pressure vessel could reach between about 1700 psig to about 2500 psig, depending on the volume of the starting feed and the temperatures reached.

Figure 6:
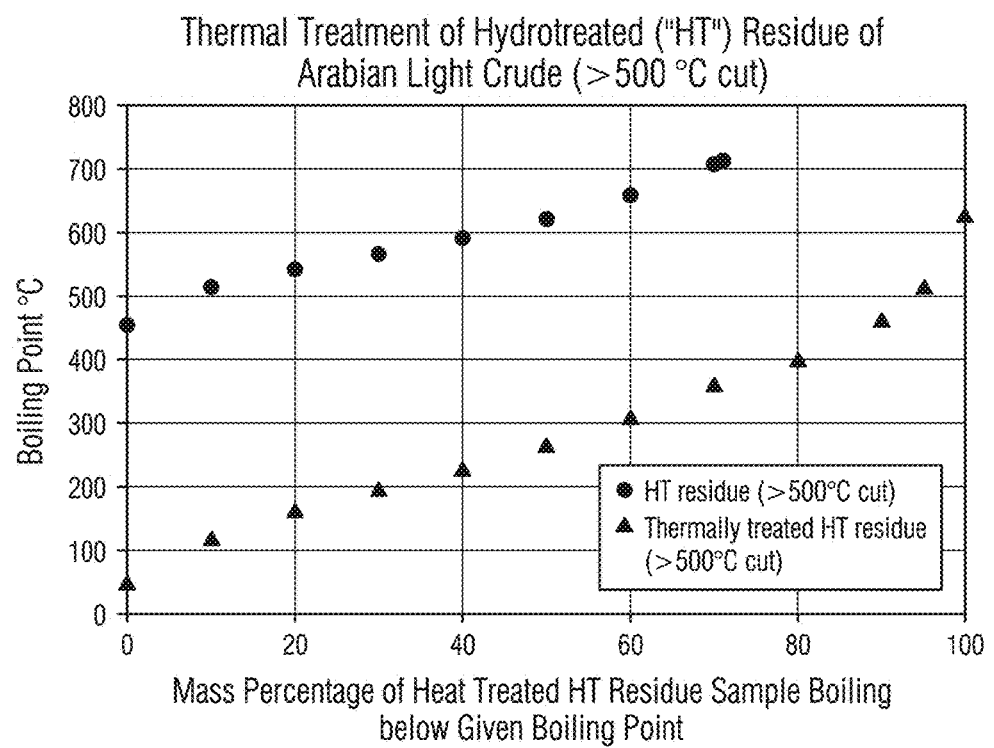
FIG. 6 is a graph showing the reduction in boiling point for a sample of hydrotreated (HT) residue of Arabian light crude oil which was thermally treated according to an embodiment of the present disclosure at a temperature of 425° C., and at a stirring rate of 650 rotations per minute (rpm) for 6 hours.

FIG. 6 is a graph showing the reduction in boiling point for a sample of hydrotreated (HT) residue of Arabian light crude oil which was thermally treated according to an embodiment of the present disclosure. As shown in FIG. 6, the untreated HT residue started with components having boiling points from about 460° C. to about 720° C. and higher. After thermal treatment, 100% of the components of the liquid cut have a boiling point less than 634° C.

Figure 7:
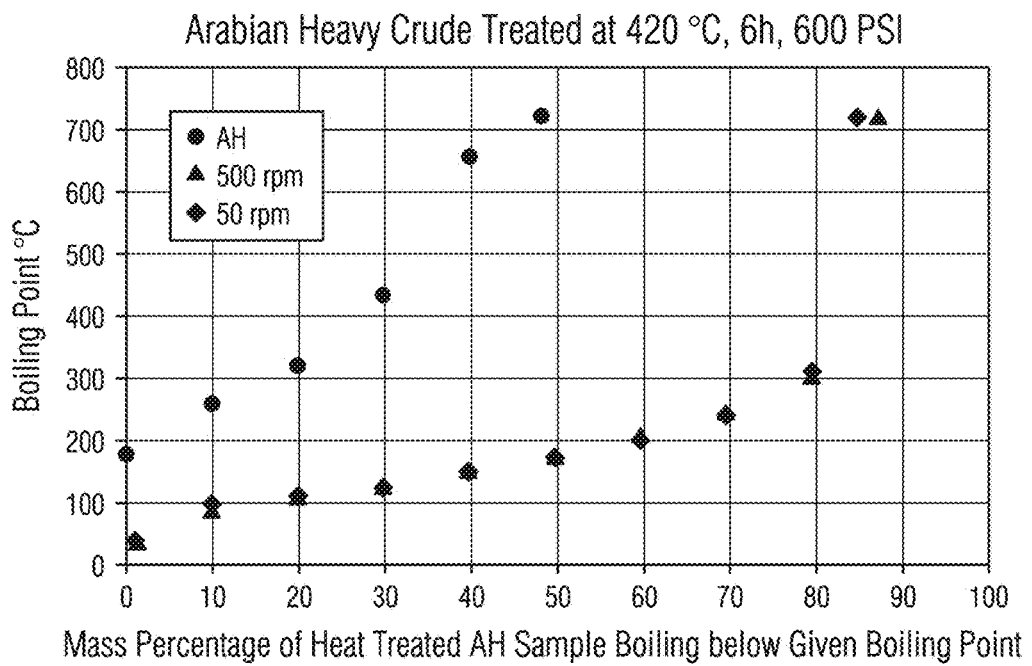
FIG. 7 is a graph showing the reduction in boiling point for a sample of Arabian heavy crude oil which was thermally treated according to an embodiment of the present disclosure.

FIG. 7 is a graph showing the reduction in boiling point for a sample of Arabian heavy crude oil which was thermally treated according to an embodiment of the present disclosure. Simulated distillation was used to characterize the thermally treated Arabian heavy crude oil, the sample being treated at 420° C. for 6 hours, and initially at 600 psig pressure using $N_2$. There is no large difference between the sample treated at 50 rpm and at 500 rpm throughout the duration of the polymerization time.

Figure 8:
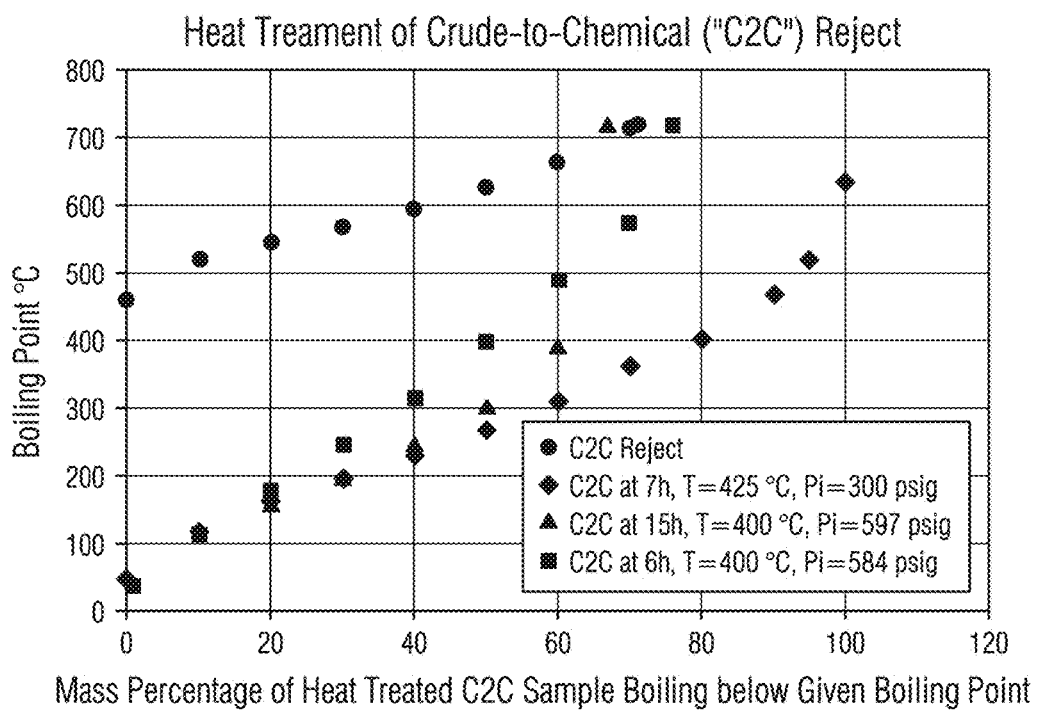
FIG. 8 is a graph showing the reduction in boiling point for a sample of C2C reject which was thermally treated according to an embodiment of the present disclosure.

FIG. 8 is a graph showing the reduction in boiling point for a sample of C2C reject material which was thermally treated according to an embodiment of the present disclosure. The greater than 500° C. boiling point residue of hydrotreated Arabian light crude was treated at different temperatures with different polymerization times. Similar behaviors as the heavy crude described previously were noticed. Liquid obtained when C2C reject was treated at a higher temperature, 425° C. with a polymerization time of 7 hours, showed 100% recovery at less than 650° C. with 90% boiling point under 500° C.

FIG. 9 is a graph showing the pressure profile of a reactor vessel during heat treatment of HT residue of Arabian light crude oil. As can be seen, the pressure increases from an initial pressure of about 600 psig to a final pressure of about 1,800 psig.

FIG. 10 is a graph showing the pressure profile of a reactor vessel during heat treatment of Arabian heavy crude oil. As can be seen, the pressure increases from an initial pressure of about 600 psig to a final pressure of about 1,900 psig.

What is claimed is:

1. A method for producing mesophase pitch, the method comprising the steps of:
    flushing a vessel with nitrogen in addition to or alternative to an inert gas to remove air and oxygen from the vessel;
    charging the vessel with a hydrocarbon feed;
    pressurizing the vessel to an initial pressure between about 290 pounds per square inch gauge (psig) to about 725 psig;
    heating the vessel to a pre-determined temperature; and
    maintaining the vessel within about 100° C. of the pre-determined temperature for an amount of time operable to upgrade the hydrocarbon feed to a product comprising mesophase pitch.

2. The method according to claim 1, where the hydrocarbon feed comprises at least one hydrocarbon selected from the group consisting of: heavy crude oil, light crude oil, and crude oil residue with a boiling point greater than about 500° C.

3. The method according to claim 1, where the step of pressurizing the vessel to the initial pressure includes pressurizing the vessel with nitrogen or an inert gas.

4. The method according to claim 3, where the step of pressurizing the vessel to the initial pressure includes the use of nitrogen.

5. The method according to claim 1, where the pre-determined temperature is between about 350° C. and about 450° C.

6. The method according to claim 1, where the pre-determined temperature is between about 400° C. and about 425° C.

7. The method according to claim 1, where the initial increased pressure is between about 550 psig and about 600 psig.

8. The method according to claim 1, where the amount of time is between about 6 hours and about 17 hours.

9. The method according to claim 1, where the pre-determined temperature is about 425° C., the initial pressure is about 600 pounds per square inch gauge (psig), and the amount of time is about 6 hours.

10. The method according to claim 1, where an asphaltene compound content of a liquid phase of the product is reduced by at least about 50% by mass relative to an asphaltene compound content of the hydrocarbon feed.

11. The method according to claim 1, where an asphaltene compound content of a liquid phased of the product is reduced by at least about 90% by mass relative to an asphaltene compound content of the hydrocarbon feed.

12. The method according to claim 1, where the steps of the method are carried out without applying any additional additives or solvents.

13. The method according to claim 12, where a metal content in a liquid phase of the product is less than a metal content in the hydrocarbon feed.

14. The method according to claim 1, where the product comprising mesophase pitch is homogeneous throughout a liquid phase and is suitable for direct crude-to-chemical applications.

15. The method according to claim 1, where the product comprising mesophase pitch includes a distinct solid phase that is at least about 90% pure mesophase pitch.

16. The method according to claim 1, where the product comprising mesophase pitch includes a distinct solid phase that is at least about 99% pure mesophase pitch.

17. The method according to claim 1, where the product comprising mesophase pitch includes a distinct liquid phase where about 80% by mass of the liquid phase exhibits a boiling point less than about 250° C.

18. The method according to claim 1, where the product comprising mesophase pitch includes a distinct liquid phase where about 90% by mass of the liquid phase exhibits a boiling point less than about 400° C.

19. The method according to claim 1, where the product comprising mesophase pitch includes a distinct liquid phase where about 90% by mass of the liquid phase exhibits a boiling point less than about 500° C.

20. The method according to claim 1, where the step of maintaining the vessel within about 100° C. of the pre-determined temperature proceeds for between about 6 hours and about 17 hours and pressure in the vessel increases to a final pressure between about 1,700 psig and about 2,500 psig.

* * * * *